United States Patent [19]

Stöhr et al.

[11] Patent Number: 4,544,737
[45] Date of Patent: Oct. 1, 1985

[54] PIPERAZINYL-TRIAZINYLNAPHTHOL-SULPHONIC ACID AZO DYES

[75] Inventors: Frank-Michael Stöhr, Burscheid; Horst Nickel, Leverkusen, both of Fed. Rep. of Germany

[73] Assignee: Bayer Aktiengesellschaft, Leverkusen, Fed. Rep. of Germany

[21] Appl. No.: 586,903

[22] Filed: Mar. 9, 1984

Related U.S. Application Data

[63] Continuation-in-part of Ser. No. 360,287, Mar. 22, 1982, abandoned.

[30] Foreign Application Priority Data

Apr. 8, 1981 [DE] Fed. Rep. of Germany ....... 3114088

[51] Int. Cl.$^4$ .................... C09B 44/00; C09B 44/02; C09B 44/08; D06P 1/08
[52] U.S. Cl. ................... 534/605; 534/603; 534/604; 534/613; 534/856; 544/198
[58] Field of Search ............ 260/153; 544/198; 534/604, 605, 613

[56] References Cited

U.S. PATENT DOCUMENTS 3,580,913  5/1971  Heimberger et al. ......... 544/198 X
4,363,761  12/1982  Pedrazzi ..................... 260/153

FOREIGN PATENT DOCUMENTS 0055583  7/1982  European Pat. Off. ......... 544/198
1419859  1/1970  Fed. Rep. of Germany ...... 260/153
7406964  9/1975  France ....................... 544/198

Primary Examiner—Floyd D. Higel
Attorney, Agent, or Firm—Sprung Horn Kramer & Woods

[57] ABSTRACT

Water-soluble triazine compounds which, in their betaine form correspond to the formula

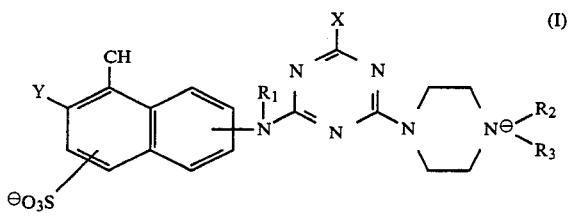

wherein
$R_1$ denotes hydrogen or alkyl,
$R_2$ and $R_3$ independently of one another denote hydrogen, alkyl, alkenyl or aralkyl,
X denotes halogen, hydroxyl, alkoxy, alkyl, aryl or an optionally monosubstituted or disubstituted amino group, the substituents of which can be involved—optionally via a hetero-atom—in cyclization, and
Y denotes hydrogen or the radical of an azo dyestuff, and wherein
the cyclic and acyclic radicals can carry further substituents, are used—when Y represents the radical of an azo dyestuff—for dyeing synthetic and natural materials, in particular paper, and—when Y represents hydrogen—for the preparation of azo dyestuffs.

4 Claims, No Drawings

PIPERAZINYL-TRIAZINYLNAPHTHOLSULPHONIC ACID AZO DYES

This is a continuation-in-part of application Ser. No. 360,287 filed Mar. 22, 1982, now abandoned.

The invention relates to water-soluble triazine compounds which, in their betaine form, correspond to the formula

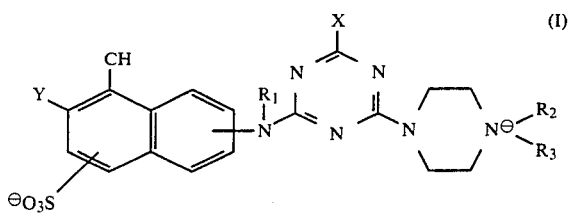

wherein

R₁ denotes hydrogen or alkyl,

R₂ and R₃ independently of one another denote hydrogen, alkyl, alkenyl or aralkyl, X denotes halogen, hydroxyl, alkoxy, alkyl, aryl or an optionally monosubstituted or disubstituted amino group, the substituents of which can be involved—optionally via a hetero-atom—in cyclisation, and Y denotes hydrogen or the radical of an azo dyestuff, and wherein the cyclic and acyclic radicals can carry further substituents, their preparation and—when Y represents the radical of an azo dyestuff—their use for dyeing synthetic and natural materials, in particular paper, and—when Y represents hydrogen—their use for the preparation of azo dyestuffs.

Compounds of the formula (I) wherein the sulphonic acid group is in the 3-position and R₁ represents hydrogen are preferred.

Compounds which should be singled out are water-soluble cationic azo dyestuffs of the formulae

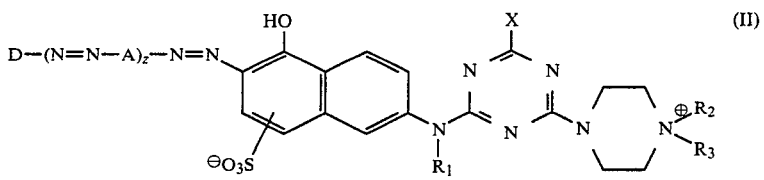

wherein

D denotes the radical of a diazo component of the benzene, naphthalene or heterocyclic series, A denotes the radical of a coupling component of the benzene or naphthalene series, z denotes 0 or 1, and X, R₁, R₂ and R₃ have the meaning of formula (I), and wherein, in the dyestuff molecule, the sum of the basic and/or cationic groups must be at least 2, and

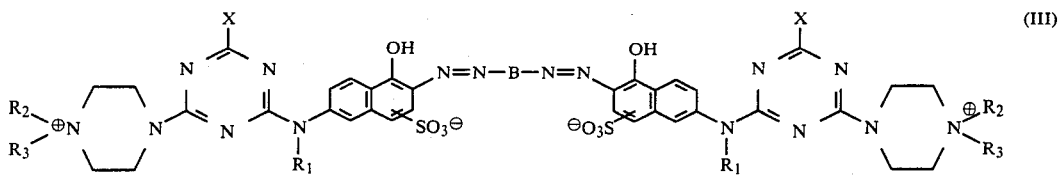

wherein

B represents the radical of an aromatic tetrazo component,

X, R₁, R₂ and R₃ have the meaning of formula (I), and wherein the sum of the basic and cationic groups in the molecule must be greater than 2, preferably greater than 3.

The number of basic and cationic groups is of decisive importance for the water-solubility of the dyestuffs, since the sulphonic acid group can form a sparingly soluble inner salt with the basic or cationic group, and only excess basic groups in the form of the acid addition salts and/or cationic groups effect the water-solubility.

In these compounds, the additional basic and/or cationic group or groups can be localised in A, D and B as well as in X. Under a basic group is understood an amino group, which can be protonized at pH-values of about 3–7.

Halogen particularly represents fluorine, chlorine or bromine.

An alkyl radical is preferably understood as meaning C₁–C₄-alkyl and an alkoxy radical is preferably understood as meaning C₁–C₄-alkoxy.

An alkenyl radical preferably has 3 or 4 C atoms.

Aryl particularly represents phenyl or naphthyl and aralkyl represents benzyl or phenylethyl.

Further suitable substituents of these radicals are preferably halogen, hydroxyl, C₁–C₄-alkoxy, cyano, amino or mono-C₁–C₄-alkylamino and di-C₁–C₄-alkylamino, or the ammonium compounds thereof, or tri-C₁–C₄-alkylammonium, and for the aromatic radicals, C₁–C₄-alkyl in addition.

X preferably represents a monosubstituted or disubstituted amino group or NH₂.

Preferred dyestuffs of the formulae (II) and (III) are those of the formulae

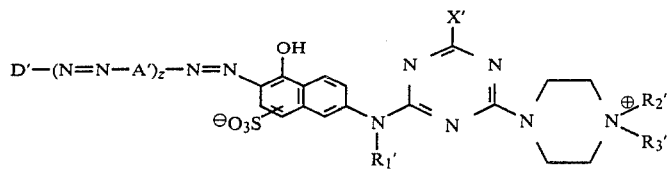 (IV)

and

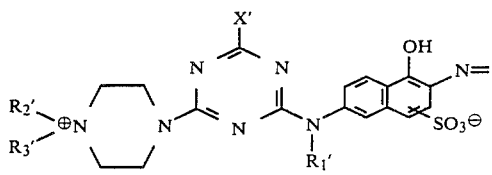 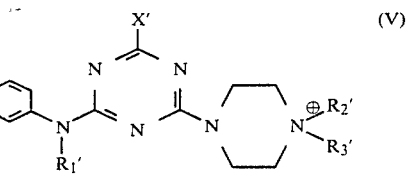 (V)

wherein $R_1'$ denotes hydrogen or methyl, $R_2'$ and $R_3'$ independently of one another denote hydrogen, $C_1$-$C_4$-alkyl, $C_3$- or $C_4$-alkenyl, benzyl or phenylethyl which can be substituted by hydroxyl, $C_1$- to $C_4$-alkoxy, halogen, cyano, amino or mono-$C_1$-$C_4$-alkylamino and di-$C_1$-$C_4$-alkylamino, or the ammonium compounds thereof, or tri-$C_1$-$C_4$-alkylammonium, and the benzyl radical and phenylethyl radical additionally by $C_1$-$C_4$-alkyl, X' denotes a radical of the formula

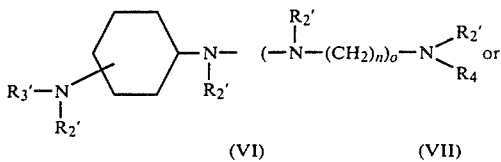 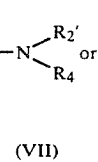 or (VI) (VII)

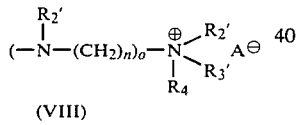

(VIII)

n denotes 2 or 3, and additionally 0 if o is 1, o denotes 0, 1 or 2, $A^\ominus$ denotes an anion, $R_4$ denotes the radical $R_2'$ and, in addition, phenyl or naphthyl which is optionally substituted by halogen, $C_1$-$C_4$-alkyl, hydroxyl, $C_1$-$C_4$-alkoxy and/or the radical

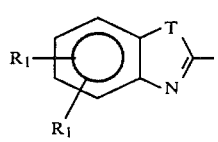 (IX)

T=S, NH benzthiazol-2-yl or isobenzthiazol-3-yl, or

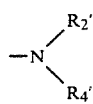

denotes a pyrrolidine, piperidine or morpholine ring or a ring of the formula

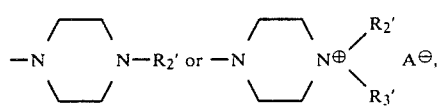

D' denotes a phenyl, naphthyl, benzthiazolyl or dibenzofuranyl radical,

A' denotes a phenylene or naphthylene radical,

B' denotes a phenylene or naphthylene radical or a radical of the formula

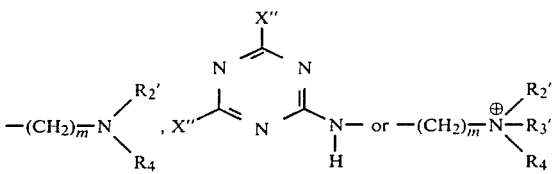

wherein $B_1$ denotes a direct bond, $-(CH_2)_p-$, $-NH-CO-$, $-O-$, $-SO_2-$, $-NHCONH-$, $-O-(CH_2)_p-O-$, $-NH-CO-(CH_2)_p-CO-NH-$, $-CO-NH-(CH_2)_p-NH-CO-$ or $$-HN\underset{N}{\overset{X''}{\underset{\|}{\overset{N}{\underset{}{\parallel}}}}}NH-$$

$R_5$ denotes hydrogen, alkyl, alkoxy or halogen, and p denotes 2 or 3, and wherein D', A' and B' can be substituted by halogen, $C_1$-$C_4$-alkyl, $C_1$-$C_4$-alkoxy, acetylamino, benzoylamino, phenoxy or the groups (VII) to (IX), $$-(CH_2)_m-N\underset{R_4}{\overset{R_2'}{\diagdown}}, X'' \underset{H}{\overset{}{}} \text{ or } -(CH_2)_m-\overset{\oplus}{N}\underset{R_4}{\overset{R_2'}{\diagdown}}R_3'$$

or a sulphonic acid group,

X'' denotes the radical X' and, in addition, the radicals

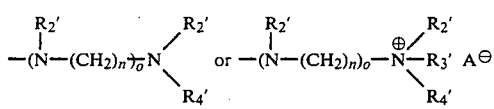

wherein

R₄' denotes phenyl or naphthyl which is optionally substituted by the radicals

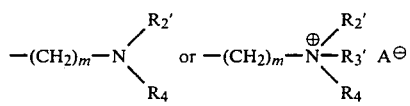

and m and z can be 0 or 1.

In the formulae (IV) and (V) preferably $R'_2$ is hydrogen and $R'_3$ is aminoethyl or amino-propyl.

The choice of the diazo or tetrazo components must be effected such that the condition of water-solubility is fulfilled, that is to say that the resulting coloured molecule contains at least one basic or cationic group more than the molecule possesses sulphonic acid groups.

Thus, if the coupling component (I) (Y=hydrogen) has a second basic or cationic group in addition to the basic or cationic group in X, any desired aromatic, carbocyclic or heterocyclic diazo or tetrazo component—which is free from anionic groups—can be used, such as, for example, aniline, aminoazobenzene, aminonaphthalene, 4,4'-diamino-benzoyl-anilide, 4,4'-diamino-3,3'-dimethyl- or -dimethoxydiphenyl and 1,2-(4,4'-diaminodiphenyl)ethane.

If, in contrast, the coupling component (I) (Y=hydrogen) has only one basic or cationic group, the aromatic, carbocyclic or heterocyclic diazo or tetrazo component must have at least one basic or cationic group in order to achieve the water-solubility, in the salt form of the basic group or of the cationic group.

Examples of suitable diazo components of this type are aniline-3- or -4-trimethylammonium chloride, methosulphate, sulphate, benzenesulphonate, tosylate, 3- or 4-aminobenzyldi- or -trimethylammonium chloride or methosulphate, or 2-aminonaphthalene-5-methylenetrimethylammonium methosulphate.

This group also includes aminoazo compounds containing optionally alkylated amino or ammonium groups which are optionally bonded via a methylene group, such as, for example,

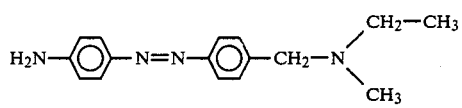

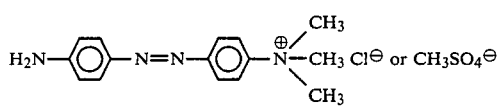

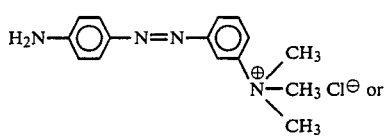

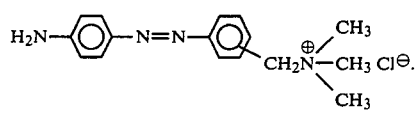

and also compounds, of the abovementioned type, in which the benzene nucleus is still further substituted by methyl, methoxy, ethoxy or chlorine, and the coupling products of 2-aminonaphthalene-5-methylenetrimethylammonium chloride with aniline or with 3-methylaniline or with 2-methoxyaniline or with 2-methoxy-5-methylaniline.

Customary colourless organic and inorganic anions, for example chloride, bromide, iodide, hydroxide, hydrogen sulphate, sulphate, nitrate, dihydrogen phosphate, hydrogen phosphate, phosphate, carbonate, methosulphate, ethosulphate, formate, acetate, propionate, benzenesulphonate and toluenesulphonate, are suitable as the anion $A^{\ominus}$.

In general, the anion is given by the preparation process. The anions can be replaced, in a known manner, by other anions. The chlorides, hydrogen sulphates, sulphates, methosulphates, phosphates, formates or acetates are preferably present.

In general, the coupling components (I) (Y=H) are prepared in a known manner, as follows: the naphthalenesulphonic acid (X), preferably the 3-sulphonic acid, is first reacted with cyanuric halide, preferably cyanuric chloride or cyanuric fluoride, to give the 1:1 compound. The X substituent is then introduced by halogen exchange, for example using ammonia or amines HX.

After introduction of the substituents X in the second stage (at 20°–50° C.), the condensation with the amino compound

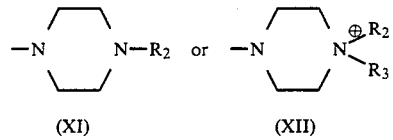

(XI)    (XII)

is carried out at 70°–95° C. in the third stage.

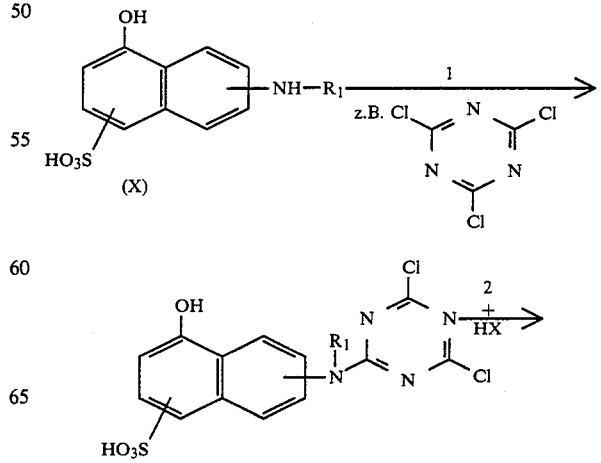

-continued

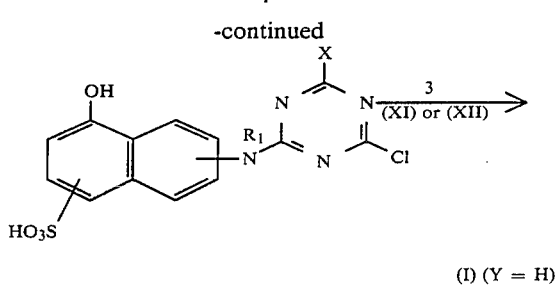

(I) (Y = H)

If X=F, Cl or Br, the reaction is carried out using (XI) or (XII) in the second stage.

Of course, it is possible to exchange the individual condensation steps and, for example, to first condense the compounds (XI) or (XII) with the cyanuric halide.

Preferred compounds (XI) are unsubstituted piperazine, N-methylpiperazine and N-(2-hydroxyethyl)-piperazine, and particularly N-(2-aminoethyl)-piperazine.

The following may be mentioned as the amines HX: $C_1$–$C_4$-mono alkylamines or dialkylamines, such as methyl-, ethyl-, chloroethyl-, propyl-, iso-propyl-, butyl-, hydroxy-ethyl-, i-propyl-, 2-methoxy-ethyl-, dimethyl-, diethyl-, di-i-propyl-, di-n-propyl-, diethanol-, di-isopropanol-, di-iso-butyl-, methyl-ethyl-, methyl-ethanol- and ethyl-ethanolamine, 3-methylaminopropionitrile, cycloalkylamines, such as pyrrolidine, piperidine, morpholine, piperazine, N-methyl-piperazine, N-(2-hydroxyethyl)-piperazine and N-(2-amino-ethyl)-piperazine, or the corresponding piperazinium salts; aralkylamines, such as benzylamine, benzyl-methylamine and benzyl-ethanolamine, which can be substituted in the phenyl nucleus by chlorine or methyl, diamines, such as ethylenediamine, N,N'-dimethylethylenediamine, 1-amino-2-diethylaminoethane, propylenediamine, N-methyl- and N,N-dimethyl- or -ethyl-propylenediamine, dipropylenetriamine, diethylenetriamine, N,N',N''-trimethyldiethylene-triamine and 1,4-diaminocyclohexane, aromatic amines, such as aniline, N-methyl-, N-ethyl- or N-hydroxyethylaniline which can be substituted in the o-, m- or p-position in the phenyl nucleus by methyl, ethyl, chlorine, methoxy or ethoxy, 1-naphthylamine, dehydrothiotoluidine or -xylidine, 2aminobenzothiazole and 3-aminoisobenzo-thiazole, and also methyl- and dimethylhydrazine.

The following may be mentioned, in addition, as the amines HX: aromatic amines, such as aniline, N-methyl-, N-ethyl- or N-hydroxyethylaniline which are substituted in the m- or p-position in the phenyl nucleus by N,N-dimethylamino or N,N-diethylamino, trimethylammonium chloride, methosulphate, acetate or tosylate, methylenedimethyl-, -diethylamino or methylenetrimethylammonium chloride, or 2-aminonaphthalene-5-methylenetrimethylammonium chloride.

The new azo dyestuffs (I) (Y=the radical of an azo dyestuff) are prepared according to customary processes known in azo chemistry (see, for example, Houben Weyl: Methoden der organischen Chemie (Methods of Organic Chemistry), Volume X/3, Georg Thieme Verlag, Stuttgart, 1965, from page 226 and page 270), by coupling diazonium or tetrazonium compounds with coupling components of the formula (I) (Y=H), preferably in an aqueous medium. If X=alkyl or aryl, only 2 replaceable halogen substituents are, of course, available in the triazine ring, there being a possible choice of first condensing (XI) or (XII), or the aminonaphtholsulphonic acid (X).

The dyestuffs are used for dyeing materials which can be dyed with cationic dyestuffs. The following may be mentioned as examples: polyacrylonitrile, acid-modified polyesters, for example polyglycol terephthalates, as described in Belgian Patent Specification No. 549,179 or U.S. Pat. No. 2,893,816, acid-modified polyamides, tanned vegetable fibres (cotton), leather and, preferably, paper. The dyestuffs are suitable for dyeing sized and unsized paper, it being possible for the paper to be prepared from bleached or unbleached pulp and for hardwood or softwood pulp, such as birch and/or pine sulphite and/or sulphate pulp, to be used.

The dyestuffs are used both as powder or granule preparations and in the form of concentrated solutions. Powder preparations are formulated in the customary manner, using extenders, such as sodium sulphate, sodium phosphate, sodium chloride or sodium acetate, in the presence of dedusting agents, or the dyestuffs are brought into commercial use directly as spray-dried preparations. Concentrated dyestuff solutions can be of aqueous or aqueous/organic type, customary additives, which are non-polluting and can be degraded as readily as possible, being preferred, such as inorganic or organic acids, preferably acetic acid, hydroxyacetic acid, formic acid, lactic acid, citric acid, methanesulphonic acid and phosphoric acid, amides, such as formamide, dimethylformamide and urea, alcohols, such as glycol and diglycol, and diglycol ethers, preferably methyl, ethyl or butyl ether.

The dyestuffs have an excellent affinity and very good general fastness properties. Paper dyeings are distinguished by very good fastnesses to wet processing as well as fastness to alum, water, acid, alcohol, milk and alkali. The fastness properties are expecially good when the dyeing is carried out in accordance with the process disclosed in U.S. Pat. No. 4,221,562. They have a surprisingly high light fastness with high clarity and intensity at the same time.

EXAMPLE 1

Ice and water are stirred, with 92 g (0.5 mol) of cyanuric chloride and 0.5 g of emulsifier L5, per 125 g, to give a fine dispersion. 110 g (1.1 mol) of N-methylpiperazine are thereafter added dropwise to the dission at 0°–5° C. in the course of 3 hours. The mixture is further stirred at 40°–45° C. for 1 hour and 0.39 mol of I acid is added. The mixture is heated to 95° C. for 3 hours. After the end of the condensation, the coupling component of the formula

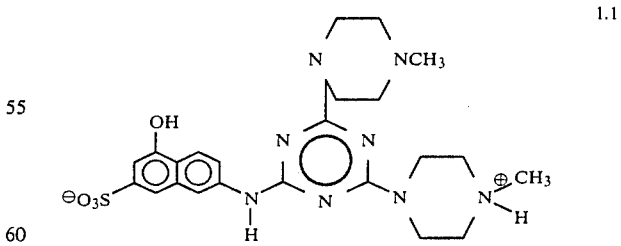

1.1 is present and is adjusted to pH 2 by acidification with 28% strength HCl and can be directly further processed for coupling, as a solution.

If the I acid is used as the first condensation component and is condensed in the 1st stage, as above, at 0°–5° C. with cyanuric chloride, it is advantageous to carry out an intermediate isolation after the 2nd stage at 40°–50° C. using aniline, N-methylaniline, 2-methylaniline, methylamine, dimethylamine, N,N-diemthylpropylenediamine or one of the other amines HX mentioned, and finally to carry out the condensation in the 3rd stage at 80°–95° C. with β-hydroxyethylpiperazine to give, for example, the coupling component 1.2

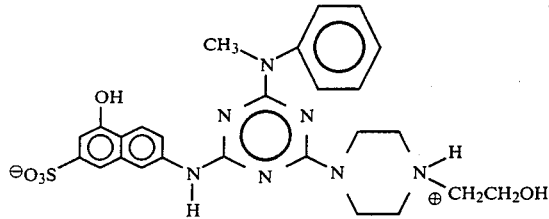

If the condensation is carried out in the third stage with an excess of piperazine, the coupling component 1.3

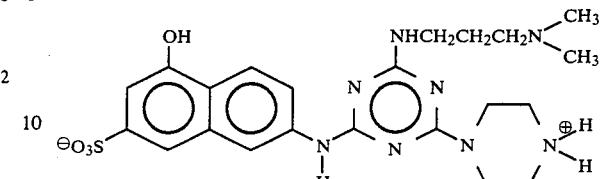

is obtained, provided that the 2nd stage was carried out with N,N-dimethylpropylenediamine.

In the table which follows, further coupling components are listed in their betaine forms:

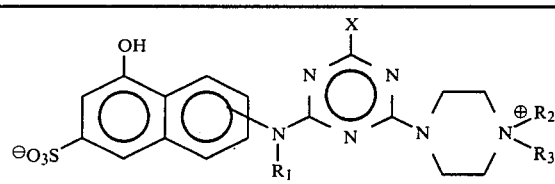

|  | Acid | HX | $R_1$ | $R_2$ | $R_3$ |
|---|---|---|---|---|---|
| 1.4 | I acid | Aniline | H | —CH₂CH₂OH | H |
| 1.5 | " | Methylamine | " | " | " |
| 1.6 | " | Dimethylamine | " | " | " |
| 1.7 | " | Diethanolamine | " | " | " |
| 1.8 | " | Diisopropanolamine | " | " | " |
| 1.9 | " | Morpholine | " | " | " |
| 1.10 | " | Piperidine | " | " | " |
| 1.11 | " | Ammonia | " | " | " |
| 1.12 | " | Ethylenediamine | " | " | " |
| 1.13 | " | H—N⌒NCH₂CH₂OH | " | " | " |
| 1.14 | " | Dimethylamine | " | —CH₃ | " |
| 1.15 | " | Diethanolamine | " | " | " |
| 1.16 | " | " | " | H | " |
| 1.17 | " | HN⌒NH | " | " | " |
| 1.18 | " | Dimethylamine | " | —CH₃ | —CH₃ |
| 1.19 | " | HN⌒N⁺(CH₃)₂ | " | " | " |
| 1.20 | " | Dimethylpropylenediamine | —CH₃ | —CH₂CH₂OH | H |
| 1.21 | Gamma acid | " | H | " | " |
| 1.22 | I acid | HN⌒NCH₂CH₂NH₂ | " | —CH₂CH₂NH₂ | " |
| 1.23 | " | Diethanolamine | " | " | " |
| 1.24 | " | Morpholine | " | " | " |
| 1.25 | " | Dimethylpropylenediamine | " | " | " |

-continued

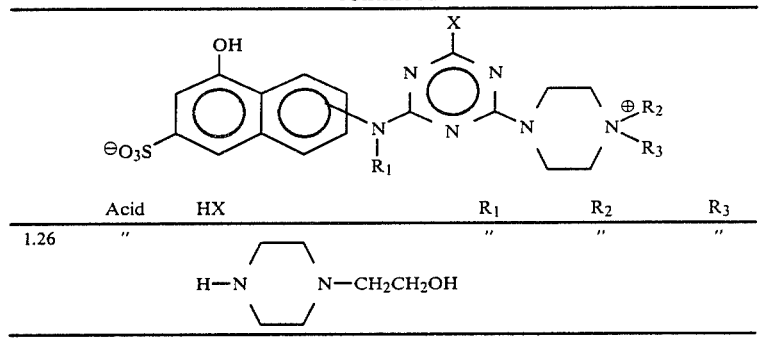

| Acid | HX | R₁ | R₂ | R₃ |
|------|----|----|----|----|
| 1.26 | " | H—N⟨ ⟩N—CH₂CH₂OH | " | " | " |

To prepare the coupling components 1.18 and 1.19, the reaction can first be carried out with methylpiperazine and the product subsequently quaternised with the customary quaternising agents. Furthermore, it is also possible to carry out the quaternisation after the coupling.

EXAMPLE 2

8.9 g (0.07 mol) of 4-methoxyaniline are dissolved in 200 ml of water using 20 ml of 28% strength HCl, and are diazotised at 0°–5° C. with 50 ml of 10% strength NaNO₂ solution. 43.7 g (0.076 mol) of the coupling component of the formula

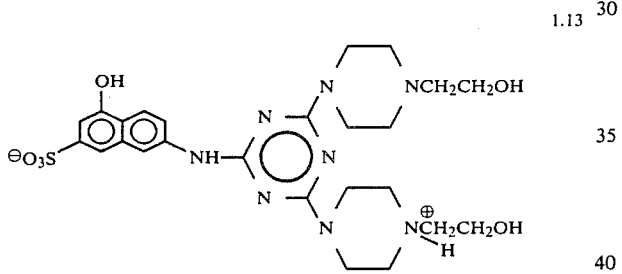

1.13 are dissolved in 200 ml of water at pH 3. The diazotisation solution is added to the above mixture and coupling is carried out at 5°–10° C. The pH of the mixture is kept at 4.5–5 with solid sodium bicarbonate. After 3 hours, the mixture is adjusted to pH 10 with 40% strength sodium hydroxide solution and the precipitated dyestuff is filtered off under suction. The paste is dissolved in 240 g of 85% strength H₃PO₄, 5 g of glacial acetic acid and 5 g of lactic acid at 50° C. and the solution is clarified. A concentrated ready-to-use solution which is stable to low temperatures and dyes paper in red shades is obtained.

If the 4-methoxyaniline is replaced by the following diazo components, valuable dyestuffs which dye paper in yellow-orange to bluish-tinged red shades are also obtained: 2-methoxyaniline, 1-amino-4-benzoylaminobenzene, 1-amino-4-acetylaminobenzene, 2- and 4-aminodiphenyl ether, 2,5-dimethoxyaniline, 2,5-dimethylaniline, 2-methoxyl-5-methylaniline, aniline, 3-chloro-4-methylaniline, 2-aminonaphthalene-5-sulphonic acid amide, 4-methylaniline, 4-aminobenzoic acid anilide, 2-(4'-aminophenyl)-6-methylbenzthiazole, 2-aminodibenzofuran, 4-chloroaniline, 2,4- or 2,5-dichloroaniline, 4-ethoxyaniline, 2-aminonaphthalene-5-methylenetrimethylammonium chloride, 2-aminonaphthalene-1-sulpho-5-methylenetrimethylammonium chloride, aniline-3- or 4-trimethylammonium chloride, 4-aminoazobenzene, 2-methyl-4-aminoazobenzene, 4-aminoazobenzene-4'-trimethylammonium chloride, 4aminoazobenzene-4'-methylene-trimethylammonium chloride, 2-methyl-4-aminobenzene-azo-2-naphthalene-5-methylenetrimethylammonium chloride, 2-(4'-amino-3'-methylphenyl)-4,6-dimethylbenzthiazole, 2-(4'-aminophenyl)-benztriazole, 2-(4'-aminophenyl)-5-methylbenzimidazole, 2-(4'-aminophenyl)-4-methylbenzimidazole and

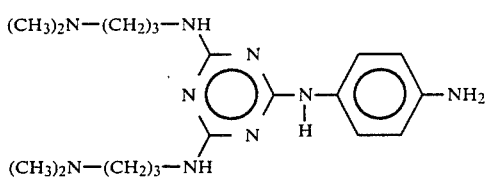

If the bis-diazo-component

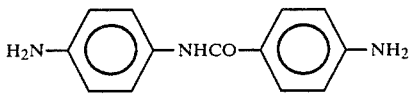

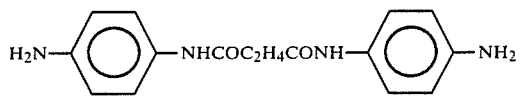

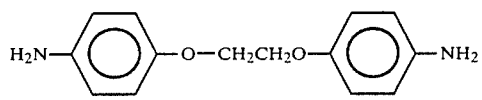

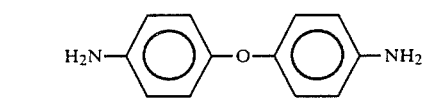

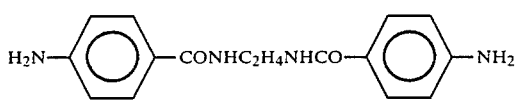

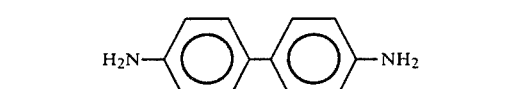

or

-continued

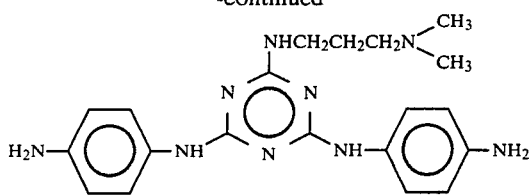

is used as the diazo component, red to violet dyestuffs are also obtained.

Using the coupling components 1.1, 1.3, 1.10, 1.12, 1.17, 1.19 and 1.20 to 1.26 and employing the above diazo components, dyestuffs result which are similar in shades to those obtained with the coupling component 1.13.

EXAMPLE 3

The solution, containing hydrochloric acid, of 25 parts (0.1 mol) of 2-aminonaphthalene-5-methylene-trimethylammonium chloride is diazotised in the customary manner with 70 ml of 10% strength NaNO$_2$ solution at 0°–5° C.

75 parts (0.11 mol) of the coupling component of the formula

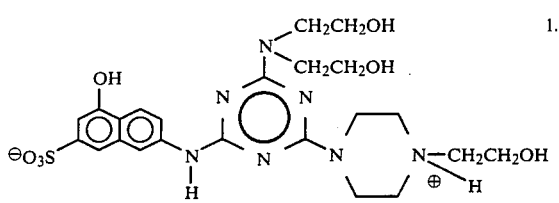

are dissolved in 400 ml of water with 40% strength NaOH and the solution is then adjusted with HCl to pH 5, the compound being precipitated. The diazotisation solution is added to the above mixture and coupling is carried out with solid NaHCO$_3$ at 5°–10° C. and pH 5.5–6. After 3 hours, the precipitated dyestuff is filtered off under suction. The paste is beaten in 400 ml of H$_2$O and the mixture is adjusted to pH 13 with 40% strength NaOH. The dyestuff is isolated, dissolved in the same quantity of formic acid at room temperature, and the solution is clarified. A concentrated ready-to-use solution which is stable to low temperatures and which dyes paper in scarlet shades is obtained.

When aniline-3- or -4-trimethylammonium chloride or aniline-3- or -4-methylenetrimethylammonium chloride is used, orange-coloured dyestuffs are obtained.

4-Amino-azobenzene-4'-trimethylammonium chloride as the diazo component gives a bluish-tinged red dyestuff.

When

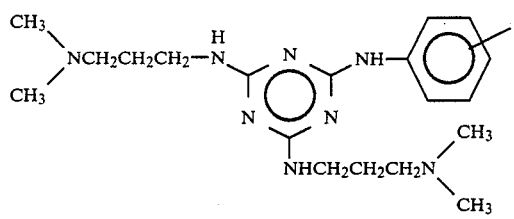

is employed, the meta-product obtained is scarlet and the para-product obtained is bluish-tinged red.

If, instead of the compound 1.7, the coupling components 1.1–1.6 and 1.8–1.26 are employed as the coupling component, with the above diazo components dyestuffs are obtained which dye paper in shades similar to those obtained with the above coupling component 1.7.

We claim:

1. A triazine dyestuff of the formula

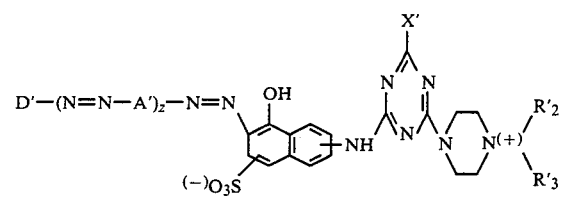

wherein

D' is phenyl or phenyl substituted by C$_1$–C$_4$-alkyl, C$_1$–C$_4$-alkoxy, acetylamino, benzoylamino, phenoxy

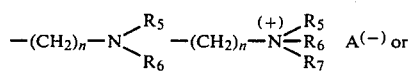

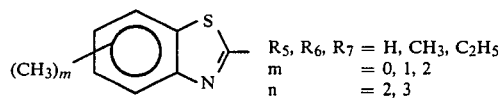

A' is phenylene or phenylene substituted by methyl or methoxy,

R'$_2$ and R'$_3$ are hydrogen, methyl, ethyl or —(CH$_2$)$_n$—Y

Y is hydroxy,

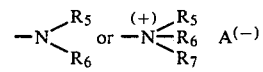

X' is

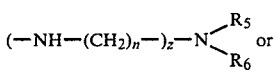

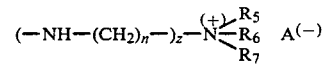

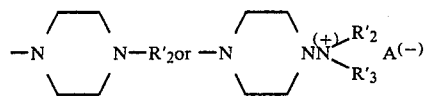

n is 2 or 3, z is 0 or 1,

A$^{(-)}$ is an anion and wherein the sum of the basic and cationic groups is at least 2.

2. A triazine dyestuff according to claim 1 wherein R'$_2$ is hydrogen or methyl, R'$_3$ is —(CH$_2$)$_n$—Y, Y is amino, dimethylamino or diethylamino.

3. A triazine dyestuff according to claim 1 of the formula

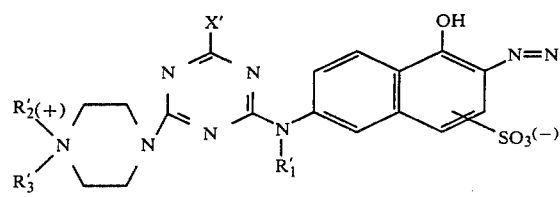
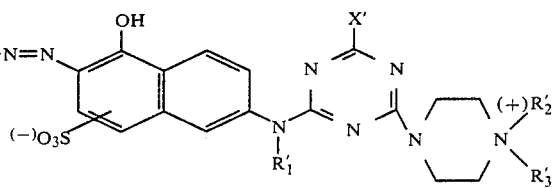

wherein
B' denotes phenylene or

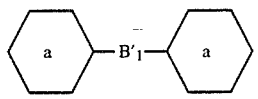

wherein
B'₁ denotes a direct bond, $-(CH_2)_{p_1}$, $-NH-CO-$, $-NH-CO-NH-$, $-O(CH_2)_{p_2}-O-$, $-NH-CO-(CH_2)_{p_2}-CO-NH-$,

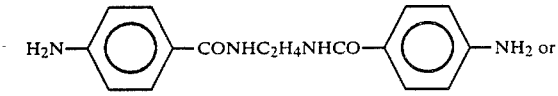

$p_1$ denotes 1, 2 or 3,
$p_2$ denotes 2 or 3 and the rings a are unsubstituted or substituted by methyl or methoxy, $R'_2$ and $R'_3$ are hydrogen, methyl, ethyl or $-(CH_2)_n-Y$,
Y is hydroxy,

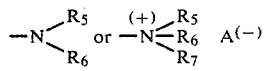

X' is

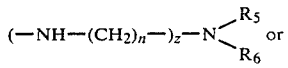

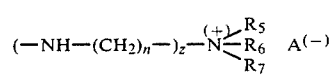

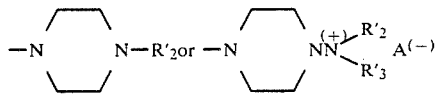

$R_5$, $R_6$, $R_7$ are H, $CH_3$ or $C_2H_5$,
n is 2 or 3,
z is 0 or 1,
$A^{(-)}$ is an anion and
wherein the sum of the basic and cationic groups are greater than 3.

4. A triazine dyestuff according to claim 1, wherein $R'_2$ is hydrogen and $R'_3$ is aminoethyl or aminopropyl.

* * * * *

UNITED STATES PATENT AND TRADEMARK OFFICE
CERTIFICATE OF CORRECTION

PATENT NO. : 4,544,737
DATED : October 1, 1985
INVENTOR(S) : Frank-Michael Stohr, et al.

It is certified that error appears in the above-identified patent and that said Letters Patent is hereby corrected as shown below:

Col. 4, line 50      Delete "$-CH_2)-$" and substitute $--(CH_2)\frac{2}{p}\underline{p}-$ Col. 9, line 2      Correct spelling of "dimethyl-"
Col. 12, line 20      After "4" insert -- - --
Col. 14, line 55 and Col. 16, line 30      End of formula delete "$>NN^{(+)}<$" and substitute $>N^{(+)}<$ --

Signed and Sealed this

Twenty-eighth Day of January 1986

[SEAL]

Attest:

DONALD J. QUIGG

Attesting Officer      Commissioner of Patents and Trademarks